United States Patent [19]

Haffer et al.

[11] 4,178,381
[45] Dec. 11, 1979

[54] C-HOMOESTRATRIENES

[75] Inventors: Gregor Haffer; Ulrich Eder; Gerhard Sauer; Rudolf Wiechert; Yukishige Nishino; Günter Neef, all of Berlin, Fed. Rep. of Germany

[73] Assignee: Schering, Aktiengesellschaft, Berlin and Bergkamen, Fed. Rep. of Germany

[21] Appl. No.: 966,162

[22] Filed: Dec. 4, 1978

[30] Foreign Application Priority Data

Dec. 9, 1977 [DE] Fed. Rep. of Germany ....... 2755578

[51] Int. Cl.² ................. A61K 31/05; A61K 31/085; A61K 31/12
[52] U.S. Cl. ................................. 424/283; 424/303; 424/308; 424/311; 424/312; 424/313; 424/314; 424/331; 424/339; 424/340; 424/346; 260/345.8 R; 260/345.9 R; 260/590 FB; 260/456 R; 260/456 A; 260/456 P; 560/106; 560/108; 560/121; 560/255; 560/107; 560/257; 568/633; 568/732
[58] Field of Search ............... 424/283, 303, 308, 311, 424/312, 313, 314, 331, 339, 340, 346; 260/345.8, 345.9, 590 FB, 456 R, 456 A, 456 P; 560/106, 108, 121, 255; 568/633, 732

[56] References Cited

U.S. PATENT DOCUMENTS

| | | | |
|---|---|---|---|
| 3,475,419 | 10/1969 | Miller | 260/239.55 |
| 3,526,665 | 9/1970 | Frey | 260/590 |
| 3,681,407 | 8/1972 | Los | 260/397.1 |

OTHER PUBLICATIONS

Annv. Rep. Med. Chem. 1969, 198.
Helv. Chim. Acta 24, 478 (1941), 295 E. 25 (1942) 1553, 1556.

Primary Examiner—Gerald A. Schwartz
Attorney, Agent, or Firm—Millen & White

[57] ABSTRACT

C-homoestratrienes of the formula

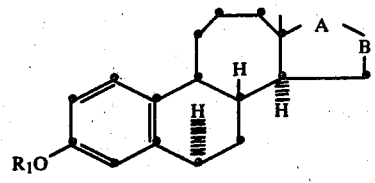

wherein

A–B is one of

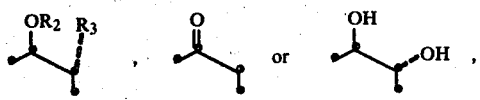

$R_1$ and $R_2$ are the same or different, and each is hydrogen, acyl, alkyl, cycloalkyl or tetrahydropyranyl; and $R_3$ is hydrogen, ethynyl or chloroethynyl; possess very good estrogenic properties.

19 Claims, No Drawings

C-HOMOESTRATRIENES

BACKGROUND OF THE INVENTION

The present invention relates to estrogenically active compounds.

SUMMARY OF THE INVENTION

It is an object of this invention to provide new derivatives of estratrienes which are estrogenically active.

Upon further study of the specification and appended claims, further objects and advantages of this invention will become apparent to those skilled in the art.

These objects have been attained by providing C-homoestratrienes of the Formula I

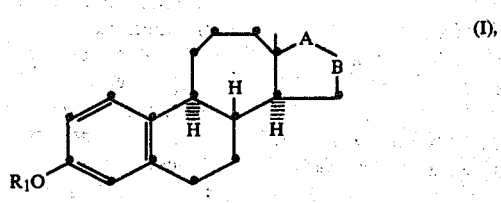

wherein $\underset{B}{\overset{A}{\diagdown}}$ is one of

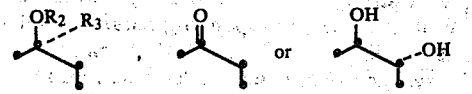

$R_1$ and $R_2$ are the same or different and each is hydrogen, acyl, alkyl, cycloalkyl or tetrahydropyranyl; and $R_3$ is hydrogen, ethynyl or chloroethynyl.

DETAILED DISCUSSION

Suitable acyl groups $R_1$ and $R_2$ are those of physiologically compatible acids. Typically, hydrocarbon carboxylic and sulfonic acids are preferred. However, there can equivalently be employed organic carboxylic and sulfonic acids of 1–16 carbon atoms, especially 1–11 carbon atoms, of the aliphatic, cycloaliphatic, aromatic, aromaticaliphatic, or heterocyclic series. These acids can be saturated or unsaturated and/or monobasic or polybasic and/or unsubstituted or substituted in the usual way. Examples of such conventional substituents include alkyl, hydroxy, alkoxy, oxo, amino or halogen.

The following carboxylic acids are suitable, for example: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, hexadecylic acid, trimethylacetic acid, diethylacetic acid, tert-butylacetic acid, cyclopentylpropionic acid, cyclohexylpropionic acid, cyclohexanecarboxylic acid, phenylacetic acid, phenoxyacetic acid, mono-, di-, and trichloroacetic acid, aminoacetic acid, diethylaminoacetic acid, piperidinoacetic acid, morpholinoacetic acid, lactic acid, succinic acid, adipic acid, benzoic acid, nicotinic acid, isonicotinic acid and furan-2-carboxylic acid.

Examples of suitable sulfonic acids include methanesulfonic acid, ethanesulfonic acid, β-chloroethanesulfonic acid, isopropanesulfonic acid, butanesulfonic acid, cyclopentanesulfonic acid, cyclohexanesulfonic acid, benzenesulfonic acid, p-toluenesulfonic acid, p-chlorobenzenesulfonic acid, N,N-dimethylaminosulfonic acid, N,N-diethylaminosulfonic acid, N,N-bis(β-chloroethyl)aminosulfonic acid and pyrrolidino-, piperidino-, piperazino-, N-methylpiperazino- and morpholinosulfonic acids.

As is evident from the diverse nature of the illustrative carboxylic and sulfonic acids named below, the exact structure of the acid residue is not critical. Therefore, contemplated equivalents of the preferred hydrocarbon carboxylic and sulfonic acids are those other types of acids named above, e.g., the heterocyclic acids, the substituted hydrocarbon acids, as well as other conventional acids whose acyl groups are in vivo hydrolyzable and physiologically acceptable.

Preferred alkyl groups $R_1$ and $R_2$ include lower alkyl groups of 1–5 carbon atoms, which can be branched or conventionally substituted. Examples of such substituents are halogen atoms and lower alkoxy groups. Especially preferred are the methyl and ethyl groups.

Suitable cycloalkyl groups $R_1$ and $R_2$ include those of 3–8 carbon atoms, among which the cyclopentyl group is preferred.

The process of this invention for preparing the novel C-homoestratrienes of Formula I comprises aromatizing in the A ring, a compound of Formula II

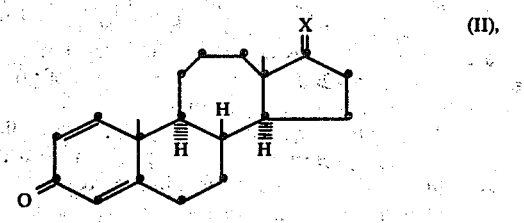

wherein

X represents $\overset{O}{\|}$ or $\diagdown\!\!\!\!\!\underset{H}{\overset{OR}{\diagup}}$ ; and R is hydrogen, acyl, alkyl, cycloalkyl or tetrahydropyranyl, as defined above for Formula I;

and, optionally, subsequently, in any desired sequence, esterifying free hydroxy groups, etherifying them in the 3- and/or 17-position; saponifying esters; cleaving ethers; oxidizing the free hydroxy group in the 17-position and optionally subsequently ethynylating or chloroethynylating it; or oxidizing the free hydroxy group in the 17-position, converting the 17-ketone into the 17-enol acetate, epoxidizing the 16,17-double bond and reducing the 16α,17α-epoxide to the C-homoestriol.

The aromatization of the A ring while eliminating the angular 19-methyl group can be effected according to known methods (see Am. Chem. Soc. 86 [1964] 742). As mentioned in this reference, previously, pyrolysis of the compounds of Formula II was conducted. However, the yield is low, even in the presence of various hydrogen donors. In contrast, good yields are obtained by using the method of the mentioned reference, i.e., reacting a 1,4-dien-3-one of general Formula II with an excess of a radical anion of lithium and biphenyl in boiling tetrahydrofuran. The addition of an acidic hydrocarbon, for example, diphenylmethane or methylnaphthalene, has a favorable effect because the methyllithium formed during the reaction is bound by this hydrocarbon.

Many processes, e.g., those discussed below, are known for conducting the aforementioned optional measures to which the aromatized product C-homoestradiol can be additionally subjected.

The esterification of the 3- and/or 17-hydroxy group can be accomplished in a conventional manner by treatment with an acid or an acid derivative in an alkaline or acidic medium. Suitable acid derivatives are esters with lower alcohols, acid halogenides, and acid anhydrides. If the compound to be esterified contains free hydroxy groups in the 3- and 17-positions, then both hydroxy groups are esterified under the usual conditions, e.g., in the presence of pyridine, dimethylaminopyridine, collidine, or dimethylformamide an elevated temperature (20°–100° C.) within 5–20 hours, or in the presence of a strong acid, e.g., trifluoroacetic acid, perchloric acid, or p-toluenesulfonic acid at room temperature within 1–10 hours. However, it is also possible to selectively esterify the 3-hydroxy group before the 17-hydroxy group using milder conditions, for example, with dimethylformamide/acid anhydride or potassium hydroxide/acid chloride within 1–5 hours at room temperature, wherein the acid moieties are the same as those mentioned above.

Examples of the esterification of the tertiary 17-hydroxy group are the reaction with an acid anhydride or halogenide in the presence of a tertiary amine at temperatures of 25°–200° C. or in the presence of potassium carbonate at room temperature.

The etherification within an alkyl or cycloalkyl group is effected preferably in the 3-position with the corresponding halogenide or sulfate in the presence of a weak base, such as potassium or sodium carbonate, in an alcohol or acetone, at boiling temperature. The etherification can also be conducted conventionally with the corresponding diazoalkane, especially with diazomethane.

Free hydroxy groups can be converted into the corresponding tetrahydropyranyl ethers with dihydropyran in the presence of a strong acid, such as p-toluenesulfonic acid or phosphorus oxychloride.

Esterified or etherified hydroxy groups can be liberated by saponification or ether cleavage, respectively. These process steps likewise take place according to conventional methods.

The saponification can be catalyzed by alkaline as well as acidic media.

Examples for the ether cleavage are the reaction of alkyl ethers with pyridine hydrochloride or pyridine/concentrated hydrochloric acid at temperatures of 180°–220° C. or with hydrohalic acids in the presence of lower carboxylic acids at temperatures of 100°–150° C. or the cleavage of tetrahydropyranyl ethers in aqueous solvents with the addition of an acid.

The oxidation of the 17-hydroxy group can be carried out in the usual way with oxidizing agents, such as chromium trioxide, for example Jones reagent (J. Chem. Soc. [London] 1946, 39). Other suitable oxidizing agents are, for example, dimethyl sulfoxide/dicyclohexylcarbodiimide and pyridine/$SO_3$.

To introduce the moiety $R_3$ as ethynyl or chloroethynyl, the 17-ketone formed during the oxidation is conventionally reacted with an organometallic ethynyl or chloroethynyl compound. Examples of suitable organometallic compounds are ethynylmagnesium bromide, ethynylzinc bromide, and potassium and lithium acetylide or potassium and lithium chloroacetylide. The organometallic compound can also be formed in situ and made to react with the 17-ketone. Thus, it is possible, for example, to treat the 17-ketone in a suitable solvent with acetylene and with an alkali metal, especially potassium or lithium, in the presence of a $C_4$- or $C_5$-alcohol or ammonia, optionally under elevated pressure. Advantageous solvents for the ethynylation and chloroethynylation are dialkyl ethers, tetrahydrofuran, dioxane, benzene, toluene, etc. The ethynylation can be conducted, in accordance with a preferred embodiment, with acetylene in tetrahydrofuran with the addition of a butyllithium solution in hexane. For the chloroethynylation, lithium chloroacetylide can be produced, for example, from 1,2-dichloroethylene in ether and from an ethereal methyllithium solution.

To prepare C-homoestriol, the 17-ketone is converted in a conventional manner, for example, with isopropenyl acetate in the presence of p-toluenesulfonic acid, into the 17-enol acetate; the latter is conveniently epoxidized with a peracid, e.g., peracetic acid or m-chloroperbenzoic acid; and the 16α,17α-epoxide is reduced. The reduction is accomplished with metal hydrides, especially complex metal hydrides, e.g., lithium aluminum hydride.

The novel C-homoestratrienes of Formula I are pharmacologically active compounds. They display, for example, a strong estrogenic activity, surpassing the effectiveness of the corresponding natural estratrienes having a six-membered C ring. With a similar spectrum of activity, the novel compounds exhibit an increased specificity and a prolonged duration of effectiveness.

The favorable pharmacological properties of the C-homoestratrienes is completely unexpected since the analogous B-homoestratrienes (Annu. Rep. Med. Chem. 1969, 198) and D-homoestratrienes (Helv. Chim. Acta 24 [1941] 478, 295 E, 25 [1942] 153, 1556) have a substantially weaker effectiveness than the corresponding natural estratrienes having a six-membered B ring or a five-membered D ring, respectively.

The C-homoestratrienes of this invention can be utilized medically in mammals, including humans, in cases of estrogen deficiency and in contraception.

Thus, for contraception, the estrogens of this invention can be employed orally, for example, in combination with a progestogen. The progestational steroid and the estrogen can be administered daily in quantitative proportions of from about 0.05 mg of progestational steroid and about 0.015 mg of the estrogen, up to about 1.00 mg of progestational steroid and about 0.050 mg of the estrogen. Methods and details of administration are as conventionally employed with the known contraceptive agent Norinyl-1 ® containing norethindrone and ethynyl estradiol.

Suitable progestogens include norethindrone (17α-ethynyl-17β-hydroxy-4-estren-3-one), norethindrone acetate, cyproterone-acetate (6-chloro-1α,2α-methylene-17α-hydroxy-4,6-pregnadien-3,20-dione-acetate), norgestrel (13β-ethyl-17α-ethynyl-17β-hydroxy-4-gonen-3-one) and lynestrenol (17α-ethynyl-17β-hydroxy-4-estren-3-one) and are disclosed for example in U.S. Pat. Nos. 2,744,122, 2,964,537, 3,234,093, 3,959,322 and 2,966,503.

The estratrienes of this invention are also suitable for parenteral application. Oily solutions or implants for parenteral application preferably contain 0.01–20 mg per dosage unit.

In cases of estrogen deficiency, the estratrienes of this invention can furthermore be used in the form of vaginal ointments, such as, for example, in atrophic vaginitis. Vaginal ointments generally contain about 0.5–20 mg of C-homoestratriene per 100 ml of ointment. Use of the compounds of this invention in treating estrogen deficiency is in accordance with the conventional methods and details employed using the know agent Linoladiol ®.

As can be seen from the foregoing, the present invention also concerns pharmaceutical preparations containing the C-homoestratrienes of Formula I, optionally in combination with a progestogen as mentioned above.

The pharmaceutical preparations are produced conventionally by converting the active agents, together with the vehicles, diluents, flavor-ameliorating agents, etc. customary in galenic pharmacy into the desired form of application, e.g., tablets, dragees, capsules, solutions, implants, ointments, etc.

The pharmacologically active compounds of Formula I can be processed in accordance with conventional methods of galenic pharmacy to produce the medicinal agents, especially for oral administration. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLES

The compounds of Formula II utilized as starting materials in accordance with this invention can be prepared by following conventional methods, for example those set forth below:

The compounds of Formula II are also novel and form a part of this invention.

Hecogenin (1) is converted to 12-spiro-2'-oxirane (2) by introducing the methylene group into the 12-position; the product is converted with sodium azide into the epimeric mixture (25R)-12α,β-azidomethyl-5α-spirostane-3β,12α,β-diol (3a), the latter is reduced with Raney nickel and hydrazine hydrate to (25R)-12α,β-aminomethyl-5α-spirostane-3β,12α,β-diol (3b), and this compound is converted in glacial acetic acid and water with sodium nitrite in water to a mixture of the isomeric C-homo-12-ketones (4 and 5) (25R)-3β-hydroxy-C-homo-5α-spirostan-12a-one (5) and -12-one (4).

Reaction of the isomeric C-homo-12-ketones with ethylene glycol, sodium hydroxide, and hydrazine hydrate solution yields (25R)-C-homo-5β-ol (6), m.p. 163° C., from which 3β-acetoxy-C-homo-5α-pregn-16-en-20-one (7), m.p. 150° C., is obtained in a three-stage process in each step under reflux temperature, with acetic anhydride, then with pyridine, acetic acid, and acetyl chloride, and at last with sidum dichromate in acetic acid.

3β-Acetoxy-C-homo-5α-pregn-16-en-20-one (7) is hydrogenated in the presence of palladium/charcoal to 3β-acetoxy-C-homo-5α-pregnan-20-one (8a), m.p. 109.8° C.; thereafter the 3β-acetoxy group is saponified, and the free 3β-hydroxy group is converted with fuming nitric acid in acetic anhydride and glacial acetic acid into the 3β-nitrooxy group. 3β-Nitrooxy-C-homo-5α-pregnan-20-one (8b) melts at 107.9° C. The compound (8b) is treated at room temperature with a peracid, e.g. m-chloroperbenzoic acid, yielding 17β-acetoxy-3β-nitrooxy-C-homo-5α-androstan (9a), m.p. 119.8° C.; the 3β-nitrooxy group of this last-mentioned compound is converted by hydrogenolysis with palladium/charcoal in glacial acetic acid into the 3β-hydroxy group, and the latter is oxidized to the 3-ketone with Jones reagent. 17β-Acetoxy-C-homo-5α-androstan-3β-ol (9b) melts at 94.3° C., and 17β-acetoxy-C-homo-5α-androstan-3-one (10) melts at 131.3° C.

17β-Acetoxy-C-homo-5α-androstan-3-one (10) is brominated for the purpose of introducing double bonds in the 1,2- and 4,5-positions, and subsequently hydrogen bromide is split off from the thus-obtained 2,4-dibromo compound with lithium bromide and lithium carbonate in dimethylformamide. The thus-obtained 17β-acetoxy-C-homo-1,4-androstadien-3-one (11a), m.p. 176.6° C., can be saponified in the 17-position in analogy to the methods indicated in the examples (11b) and can then be etherified, esterified, or oxidized. For example, it is possible to produce, from (11b), with dihydropyran, 17β-tetrahydropyranyloxy-C-homo-1,4-androstadien-3-one (11c). The 17-tetrahydropyranyloxy compound (11c) is preferred for use as a starting material, because the tetrahydropyranyl ether can be readily cleaved after the aromatization according to this invention, and the free 17-hydroxy group is then available for additional reactions. It is also possible to use, for an intermediary protection of the 17-hydroxy group, other α, β-unsaturated ethers, such as, for example, dihydrofuran and α-ethoxyethylene.

Any 17β-acetoxy-C-homo-4,6-androstadien-3-one (12) concomitantly produced during the bromination and subsequent splitting off of hydrogen bromide can be separated by chromatography.
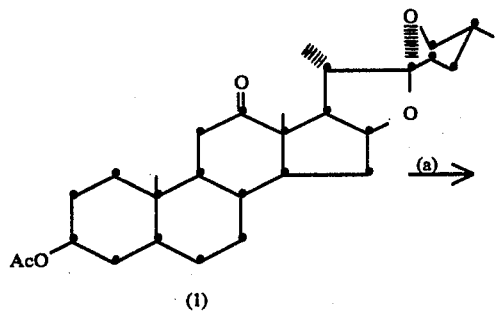
(1)
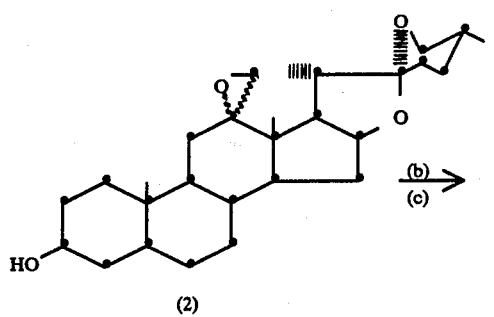
(2)
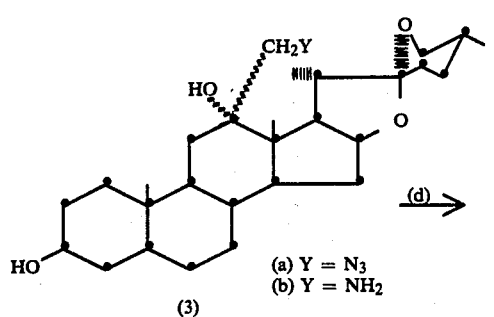
(a) Y = N₃
(b) Y = NH₂
(3)
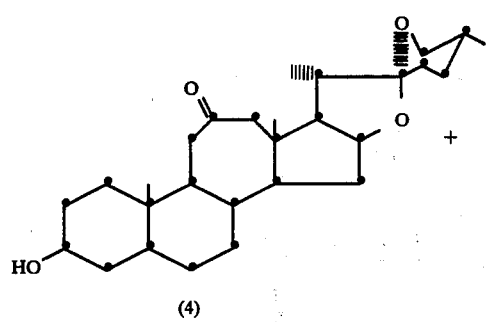
+
(4)
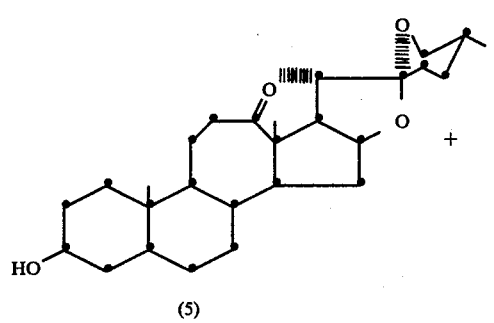
+
(5)
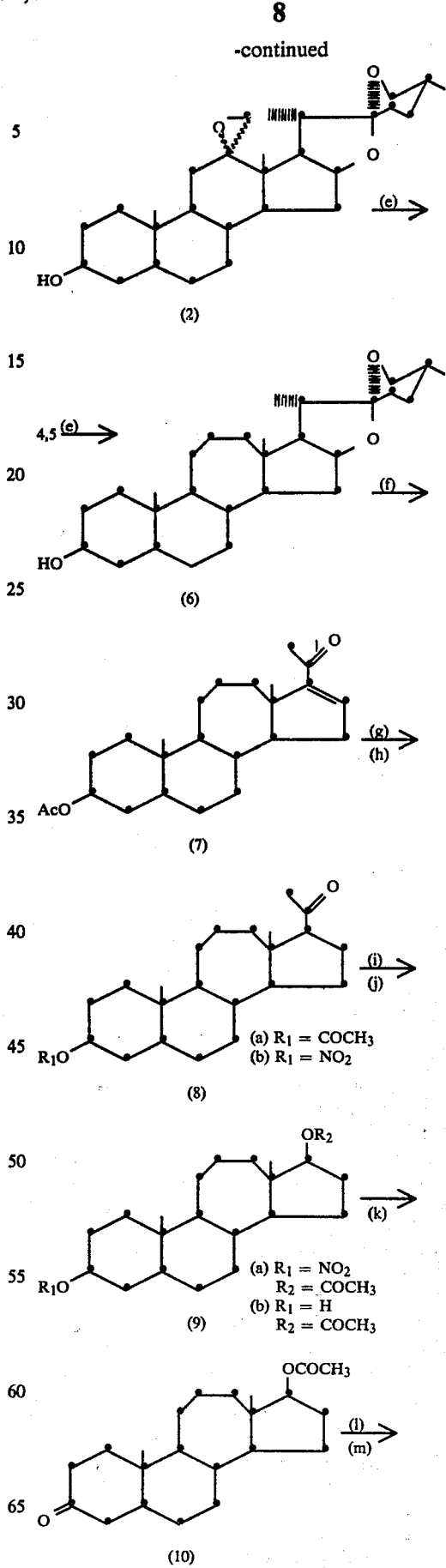
(2)
(6)
(7)
(8)
(a) R₁ = COCH₃
(b) R₁ = NO₂
(9)
(a) R₁ = NO₂, R₂ = COCH₃
(b) R₁ = H, R₂ = COCH₃
(10)

-continued

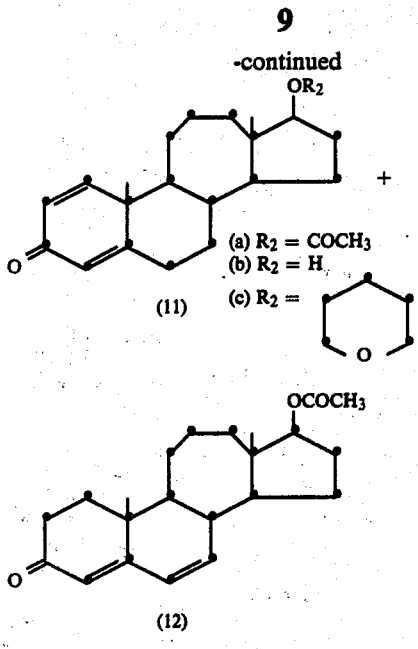

(11)
(a) $R_2 = COCH_3$
(b) $R_2 = H$
(c) $R_2 = $ [tetrahydropyranyl]

(12) [structure with OCOCH₃]

EXAMPLE 1

Under a nitrogen atmosphere, 60 g. biphenyl, dried over phosphorus pentoxide, is dissolved in 500 ml. of anhydrous tetrahydrofuran freshly distilled over lithium aluminum hydride, and 2.25 g. of lithium, cut under pentane, is added thereto. Once the solution has assumed a green color under agitation, the solution is heated to 65° C. and stirred for 15 minutes. A solution of 24 g. of 17β-tetrahydropyranyloxy-C-homo-1,4-androstadien-3-one in 350 ml. of tetrahydrofuran is combined with 11 ml. of diphenylmethane, and this solution is gradually introduced dropwise into the lithium biphenyl complex solution, heated to 65° C. The mixture is stirred for 3 hours at this temperature and then cooled with ice water to 5° C. After adding 5 ml. of methanol and 30 ml. of 2N sulfuric acid, the mixture is stirred into ice water and extracted with methylene chloride. The concentrated, moist reaction mixture is taken up in 200 ml. of acetone and 50 ml. of methanol and allowed to stand overnight with 200 ml. of a mixture of 70% acetone and 30% 2N sulfuric acid at room temperature. After evaporating half the volume under vacuum, the remainder is poured under agitation into ice water saturated with sodium bicarbonate, extracted with methylene chloride, washed with water, and dried over magnesium sulfate. The residue of the evaporation is chromatographed on silica gel in accordance with the gradient method (hexane/ethyl acetate 99:1 against 85:15), thus obtaining 14 g. of C-homoestradiol as an oil.

A sample crystallized from methanol melts at 157.0° C.

$[\alpha]_D^{20} = +128°$ (c=0.500 in chloroform).

Preparation of the Starting Material:

(a) 150 g. of hecogenin and 95 g. of trimethylsulfonium iodide are suspended in 1,000 ml. of anhydrous dimethylformamide and cooled with ice water. Under a nitrogen atmosphere and vigorous agitation, 55 g. of potassium tert.-butylate is added in incremental portions within 3 hours, and the mixture is stirred for another 6 hours at 40° C. The reaction mixture is stirred into ice water, the precipitate is filtered off, washed neutral with water, and dried in a vacuum drying chamber at 50° C., thus obtaining 148.5 g. of (12RS,25R)-5α-spirostan[12-spiro-2']oxiran-3β-ol (2).

Crystallization from ethyl acetate yields the 12S-oxirane, m.p. 211.6° C.

$[\alpha]_D^{20} = -18.1°$ (chloroform; c=1.005).

(b) 145 g. of the compound (2) described in (a), 50 g. of sodium azide, 110 ml. of water, and 1,000 ml. of dimethylformamide are heated under agitation to 100° C. for 8 hours. Under the processing conditions set out in (a), 156 g. of a crystalline mixture of epimers is obtained, (25R)-12α,β-azidomethyl-5α-spirostane-3β,12α,β-diol (3a) (proportion about 35:65 in accordance with NMR). By preparative layer chromatography (methylene chloride/ethyl acetate 60:40), (25R)-12α-azidomethyl-5α-spirostane-3β,12β-diol is obtained, m.p. 219.5° C.

$[\alpha]_D^{20} = -44.8°$ (chloroform; c=1.000) as well as the more polar compound (25R)-12β-azidomethyl-5α-spirostan-3β,12α-diol, m.p. 239.6° C.

$[\alpha]_D^{20} = -41.4°$ (chloroform; c=1.020).

(c) 150 g. of the epimer mixture (3a) described in (b) is dissolved in 1,700 ml. of ethanol and combined with 20 g. of ethanol-moist Raney nickel. Under ice water cooling and agitation, 1,400 ml. of 80% hydrazine hydrate solution is added dropwise to the reaction mixture, and the latter is agitated for another 5 hours at room temperature and then heated for another 4 hours to 70° C. After cooling, the mixture is filtered off from the catalyst and washed with methylene chloride. The moist residue of the evaporation is utilized in the subsequent stage. A sample of (25R)-12β-aminomethyl-5α-spirostane-3β,12α-diol (3b), crystallized from ethanol, melts at 252.7° C.

$[\alpha]_D^{20} = -28.1°$ (chloroform; c=1.015).

(d) The crystalline evaporation residue according to (c) is taken up in a mixture of 1,100 ml. of glacial acetic acid and 300 ml. of water. Under ice water cooling and while passing nitrogen through the reaction mixture, a solution of 95 g. of sodium nitrite in 260 ml. of water is added dropwise. The mixture is allowed to warm up to room temperature, then agitated while passing nitrogen therethrough overnight, and the reaction mixture is poured into five times the amount of ice water. The filtered-off precipitate is washed with water, taken up in methylene chloride, and dried over magnesium sulfate. The crude product is again heated with 20 g. of sodium azide in aqueous dimethylformamide and worked up as described under (b) in order to convert compound (2), produced during the reaction, into compound (3a), which can be more readily separated by chromatography. Subsequent gradient chromatography (hexane/ethyl acetate 90:10 against 65:35) on 50 times the amount of silica gel yields 92 g. of a mixture of (25R)-3β-hydroxy-C-homo-5α-spirostan-12a-one (5) and the isomeric 12-ketone (4) in a ratio of about 25:75 (in accordance with NMR and/or GC).

(e) 45 g. of the C-homoketones (4) and (5), 500 ml. of ethylene glycol, 50 g. of pulverized sodium hydroxide, and 150 ml. of 80% hydrazine hydrate solution are heated for 2 hours under agitation to 150° C. During the subsequent heating of the heating bath to 235° C., glycol, hydrazine hydrate, and the water of reaction are gradually removed by distillation during the course of 4 hours. After cooling to room temperature and adding 5 liters of a mixture of methanol/NaCl-saturated ice water (proportion 1:9), the mixture is stirred for 2 hours. After the precipitate has been allowed to settle, it is vacuum-filtered, washed neutral, and dried in a vacuum drying chamber at 50° C. Crystallization from ether yields 28 g. of (25R)-C-homo-5α-spirostan-3β-ol (6), m.p. 163° C.

$[\alpha]_D^{20} = -55.4°$ (chloroform; c=0.920).

(f) 58 g. of C-homotigogenin (6) is heated under reflux for 30 minutes in 250 ml. of acetic anhydride. The mixture is cooled by ice water and then 11.5 ml. of pyridine, 8 ml. of acetic acid, and 10 ml. of acetyl chloride are added dropwise in succession to the reaction mixture. The latter is refluxed for 3 hours, and one-third of the volume is distilled off. Subsequently a solution of 38 g. of sodium dichromate in 595 ml. of acetic acid is added at room temperature. The mixture is stirred for 10 minutes, 3.75 g. of sodium sulfite is added, the mixture is again stirred for 10 minutes and heated for 2 hours under reflux. The residue of the evaporation, obtained under vacuum, is combined with ice water and extracted with chloroform. The chloroform extract is washed in succession with saturated aqueous sodium bicarbonate solution and water and dried over magnesium sulfate. The crude product is filtered on 10 times the amount of silica gel with hexane/ethyl acetate (85:15), concentrated, and crystallized from chloroform/ether/hexane.

Yield: 26 g. of 3β-acetoxy-C-homo-5α-pregn-16-en-20-one (7), m.p. 150.3° C. UV (methanol): 240 nm. (ε=9,750)

$[\alpha]_D^{20} = +76.2°$ (chloroform; c=0.925).

(g) 25 g. of compound (7) described in (f) is hydrogenated in 850 ml. of ethyl acetate with 2.8 g. of palladium/charcoal. The stoichiometric hydrogen volume is absorbed within 30 minutes. After removing the catalyst by filtration, crystallization of the evaporation residue from ether/pentane yields 21.5 g. of 3β-acetoxy-C-homo-5α-pregnan-20-one (8a), m.p. 109.8° C.

$[\alpha]_D^{20} = +42.2°$ (chloroform; c=1.005).

(h) 20 g. of compound (8a) is saponified with 1 g. of sodium methylate in 200 ml. of methanol at room temperature. After precipitation into ice water, the mixture is worked up as described in (a). The dried crude product is dissolved in 350 ml. of acetic anhydride and 125 ml. of glacial acetic acid and cooled to −20° C. At this temperature, 140 ml. of fuming nitric acid is added dropwise. The mixture is stirred for 90 minutes and gradually poured into 10 l. of ice water under agitation. The chloroform extracts are washed neutral with bicarbonate solution and water in sequence, and then dried over sodium sulfate. The crude 3β-nitrooxy-C-homo-5α-pregnan-20-one (8b) (18.8 g.) is utilized without purification in the subsequent stage. A sample crystallized from diisopropyl ether/hexane melts at 107.9° C.

$[\alpha]_D^{20} = +49.2°$ (chloroform; c=1.035).

(i) 18 g. of 3β-nitrooxy-C-homo-5α-pregnan-20-one (8b) is stirred with .37 g. of 95% m-chloroperbenzoic acid in 200 ml. of anhydrous methylene chloride for 30 hours at room temperature. The mixture is poured on ice, extracted with chloroform, concentrated to 30 ml. of solution, and shaken three times with saturated sodium bisulfite solution and then with water. The residue from the evaporation is taken up in 50 ml. of methanol, and the solution is gradually stirred into an aqueous slurry of sodium bicarbonate. The crude product, worked up as set forth in (h), is chromatographed with hexane/ethyl acetate 99:1 against 95:5 on 70 times the amount of silica gel, thus obtaining 12.4 g. of 17β-acetoxy-3β-nitrooxy-C-homo-5α-androstane (9a), m.p. 119.8° C.

$[\alpha]_D^{20} = -1.1°$ (chloroform; c=1.005).

(j) 21.4 g. of (9a) is exhaustively hydrogenated with 4 g. of 10% palladium/charcoal in 600 ml. of glacial acetic acid. The filtered-off catalyst is washed with ethyl acetate; the filtrate is evaporated to dryness under vacuum, taken up in methylene chloride, washed neutral, and dried, thus obtaining 18.5 g. of crude 17β-acetoxy-C-homo-5α-androstan-3β-ol (9b). Yield after crystallization from ether/hexane: 13.9 g., m.p. 94.3° C.

$[\alpha]_D^{20} = -0.5°$ (chloroform; c=1.000).

(k) 13.5 g. of (9b) is dissolved in 400 ml. of acetone distilled over phosphorus pentoxide and titrated under ice water cooling with Jones solution. The mixture is then stirred into ice water saturated with bicarbonate solution and extracted with ether. The dried organic phases are evaporated and the residue crystallized from ether/pentane, thus obtaining 11.7 g. of 17β-acetoxy-C-homo-5α-androstan-3-one (10), m.p. 131.3° C.

$[\alpha]_D^{20} = +21.5°$ (chloroform; c=1.005).

(l) 34.5 g. of 17β-acetoxy-C-homo-5α-androstan-3-one (10) is dissolved in 1 l. of chloroform, combined with two drops of a 38% hydrobromic acid in glacial acetic acid and cooled with ice water. Under vigorous agitation 10.5 ml. of bromine in 100 ml. of glacial acetic acid is added dropwise thereto and the mixture is stirred for 90 minutes under ice water cooling. The reaction mixture is then poured into ice water, extracted with methylene chloride, the organic phases are washed neutral in succession with bicarbonate solution and water, dried over sodium sulfate, and concentrated on a forced circulation evaporator at room temperature. The residue is taken up in 400 ml. of anhydrous dimethylformamide.

After the addition of 10 g. of anhydrous lithium bromide and 15 g. of anhydrous lithium carbonate, the brominated 3-ketone (10) is heated under an inert gas for 3 hours in a bath preheated to 115° C. After cooling, the mixture is stirred into aqueous saturated sodium dihydrogen phosphate solution and extracted with ether. By repeated chromatography on silica gel with hexane/ethyl acetate 75:25 against 55:45 and crystallization from ether/hexane, 10.2 g. of 17β-acetoxy-C-homo-4,6-androstadien-3-one (12) is obtained, m.p. 111.1° C.

UV: 284 nm. (ε=27,400) $[\alpha]_D^{20} = +102.4°$ (chloroform; c=1.000) in addition to 22.5 g. of the polar 17β-acetoxy-C-homo-1,4-androstadien-3-one (11a), m.p. 176.6° C. UV: 244 nm. (ε=16,000) $[\alpha]_D^{20} = +52.2°$ (chloroform; c=1.010).

(m) 21.4 g. of 17β-acetoxy-C-homo-1,4-androstadien-3-one (11a) is saponified with 1 g. of sodium methylate in 200 ml. of methanol at room temperature and worked up as set forth in (a). The dried 17β-hydroxy compound (11b) is dissolved in 250 ml. of freshly distilled tetrahydrofuran. Under ice water cooling 30 ml. of freshly distilled dihydropyran and 0.15 ml. of phosphorus oxychloride are added thereto in succession, and the mixture is stirred overnight at room temperature. The reaction mixture is stirred into dilute bicarbonate solution and extracted with methylene chloride. The organic phases are washed neutral with water and dried with magnesium sulfate. After the solvent has been evaporated under vacuum, 24 g. of 17β-tetrahydropyranyloxy-C-homo-1,4-androstadien-3-one (11c) is obtained.

EXAMPLE 2

1.4 g. of lead(II) acetate and 10 ml. of acetic anhydride are added to 3 g. of 3,17β-dihydroxy-C-homo- 1,3,5(10)-estratriene (C-homoestradiol) in 30 ml. of dimethylformamide. The mixture is agitated for 4 hours at room temperature, then poured into saturated bicarbonate solution, stirred for 2 hours, and extracted with methylene chloride. The organic phase is washed, dried over magnesium sulfate, and evaporated under vacuum. Purification by chromatography on silica gel yields 2.9 g. of 3-acetoxy-C-homo-1,3,5(10)-estratrien-17β-ol as an oil.

$[\alpha]_D^{20} = +100°$ (dioxane; c=0.780) = +118.3° (chloroform; c=0.435).

EXAMPLE 3

2.5 g. of 3-acetoxy-C-homo-1,3,5(10)-estratrien-17β-ol is oxidized—as described in Example 1 (k). Crystallization from diisopropyl ether yields 2.1 g. of 3-acetoxy-C-homo-1,3,5(10)-estratrien-17-one, m.p. 92.1° C.

$[\alpha]_D^{20} = +199.6°$ (chloroform; c=0.500).

EXAMPLE 4

1.0 g. of 3-acetoxy-C-homo-1,3,5(10)-estratrien-17-one is allowed to react in 50 ml. of methanol with one drop of 70% aqueous perchloric acid for 90 minutes at room temperature. The reaction mixture is combined with saturated bicarbonate solution, extracted with chloroform, the chloroform phase washed with water, and dried over magnesium sulfate. Crystallization of the evaporation residue from diisopropyl ether/hexane yields 0.67 g. of C-homoestrone, m.p. 243.7° C.

$[\alpha]_D^{20} = +228.3°$ (chloroform; c=0.840).

EXAMPLE 5

0.3 g. of C-homoestrone and 0.5 g. of anhydrous potassium carbonate is heated under reflux with 1 ml. of methyl iodide in 10 ml. of anhydrous acetone for 6 hours. After cooling, the mixture is poured into saturated sodium dihydrogen phosphate solution and extracted with ethyl acetate. The organic phase is washed with water, dried over magnesium sulfate, and concentrated, thus obtaining 0.29 g. of 3-methoxy-C-homo-1,3,5(10)-estratrien-17-one, m.p. 157.1° C.

$[\alpha]_D^{20} = +216.4°$ (c=0.500 in chloroform).

EXAMPLE 6

0.280 g. of C-homoestradiol, 1.2 g. of the methyl ester of valeric acid (0.7 ml.), and 90 mg. of p-toluene-sulfonic acid are heated for 5 hours under nitrogen to 120° C. After cooling, 10 ml. of toluene is added thereto, the mixture is stirred intensively with saturated bicarbonate solution, washed with water, concentrated, the residue taken up in 10 ml. of methanol, and, after the addition of 0.500 g. of potassium carbonate in 2 ml. of water, agitated for 3 hours at room temperature, in order to saponify the 3-valerate. After the addition of 0.7 ml. of acetic acid in 50 ml. of ice water, the mixture is extracted with ethyl acetate, washed with water, and the organic phase, which has been dried over magnesium sulfate, is concentrated under vacuum at a bath temperature of 30° C. The purification of the product by chromatography on silica gel yields 0.325 g. of 17β-valeryloxy-C-homo-1,3,5(10)-estratrien-3-ol as a colorless oil.

UV [in methanol]: 279 nm. ($\epsilon$=2,010)
IR [in KBr]: 1735 cm$^{-1}$ (>C=O).

EXAMPLE 7

0.300 g. of 3-acetoxy-C-homo-1,3,5(10)-estratrien-17β-ol, 1.5 ml. of pyridine, and 0.285 g. of enanthic anhydride are stirred for 6 hours at 105° C. under nitrogen. After cooling to 90° C. and the addition of 0.3 ml. of water, the mixture is stirred for 15 minutes at 100° C., allowed to cool, and 50 ml. of water is added thereto. The mixture is shaken out with ether, and the ether phase is washed with water, concentrated under vacuum, taken up in 10 ml. of methanol, and under ice water cooling 0.2 g. of potassium carbonate in 0.5 ml. of water is added thereto and the mixture is stirred for 3 hours at 20° C. Thereafter the procedure is continued as described in Example 6, thus isolating 0.306 g. of oily 17β-heptanoyloxy-C-homo-1,3,5(10)-estratrien-3-ol.

UV [in methanol]: 280 nm. ($\epsilon$=2,000)
IR [in KBr]: 1740 cm$^{-1}$ (ester carbonyl group).

EXAMPLE 8

0.525 g. of C-homoestradiol, 2.5 ml. of the methyl ester of undecanoic acid, and 0.250 g. of p-toluenesulfonic acid are stirred for 6 hours under nitrogen at 105° C. The reaction mixture is worked up and partially saponified analogously to Example 6, thus isolating 0.655 g. of 17β-undecanoyloxy-C-homo-1,3,5(10)-estratrien-3-ol as an oily product.

UV [in methanol]: 280 nm. ($\epsilon$=2,030)
IR [in KBr]: 1745 cm$^{-1}$ (ester carbonyl group).

EXAMPLE 9

Under agitation and ice water cooling, 0.250 g. of cyclopentylpropionyl chloride is added to 0.300 g. of 3-acetoxy-C-homo-1,3,5(10)-estratrien-17β-ol in 1.6 ml. of anhydrous pyridine, and the mixture is stirred overnight at room temperature. Water is added to the mixture, and the latter is shaken out with ether; the ether phase is washed with water, concentrated under vacuum, and the residue of the evaporation is further processed as described in Example 7, thus obtaining 0.330 g. of 17β-(3-cyclopentylpropionyloxy)-C-homo-1,3,5(10)-estratrien-3-ol as an oil.

UV [in methanol]: 280 nm. ($\epsilon$=2,000)
IR [in KBr]: 1735 cm$^{-1}$ (>C=O).

EXAMPLE 10

0.280 g. of C-homoestradiol in 5 ml. of dioxane is added to a solution of 0.670 g. of potassium hydroxide in 15 ml. of water. At room temperature, 0.7 ml. of benzoyl chloride is added dropwise and the mixture is stirred for 2 hours. Thereafter, the mixture is shaken out with ether, washed neutral with water, and dried over magnesium sulfate. Crystallization of the evaporation residue from methanol yields 0.340 g. of 3-benzoyloxy-C-homo-1,3,5(10)-estratrien-17β-ol, m.p. 163.7° C.

UV [in methanol]: 230 nm. ($\epsilon$=18,600)
IR [in KBr]: 1720 cm$^{-1}$ (>C=O)
$[\alpha]_D^{20} = +106.2°$ (c=1.04 in chloroform).

EXAMPLE 11

40 ml. of anhydrous tetrahydrofuran is used to pass acetylene therethrough for 30 minutes under ice water cooling. The acetylene has previously been passed through paraffin, concentrated sulfuric acid, and anhydrous tetrahydrofuran. Under further cooling, 10 ml. of a 1.65-molar butyllithium solution in hexane is added within 10 minutes to the reaction mixture. The mixture is flushed with 2 ml. of anhydrous pentane, and acetylene is conducted for another 45 minutes through the cooled solution.

Thereafter, 0.500 g. of 3-acetoxy-C-homo-1,3,5(10)-estratrien-17-one is dissolved in 20 ml. of anhydrous tetrahydrofuran and added dropwise to the reaction solution within 10 minutes. While passing acetylene through the solution, the latter is allowed to react for 20 minutes, then decomposed with saturated ammonium chloride solution under cold conditions, and extracted with chloroform, thus obtaining by evaporation of the organic phases, washed with water and dried over sodium sulfate, 0.418 g. of a crude product which, after crystallization from ether/hexane yields 0.375 g. of 17α-ethynyl-C-homo-1,3,5(10)-estratriene-3,17β-diol, m.p. 184.9° C.

$[α]_D^{20} = +76.4°$ (c=0.450 in dioxane).

EXAMPLE 12

Method A:

Under nitrogen, 0.350 g. of potassium tert.-butylate is suspended in 5 ml. of tetrahydrofuran distilled over lithium aluminum hydride. Acetylene is introduced for 1 hour into the suspension, cooled to −15° C. At this point in time, 0.139 g. of 3-methoxy-C-homo-1,3,5(10)-estratrien-17-one (according to Example 5) is added, the mixture is flushed with 1 ml. of tetrahydrofuran, stirred for another 2 hours under the introduction of acetylene at −15° C., then combined with saturated aqueous sodium dihydrogen phosphate solution, and extracted with methylene chloride. After the mixture has been worked up as described in Example 11, crystallization from ether/pentane yields 0.103 g. of 17α-ethynyl-3-methoxy-C-homo-1,3,5(10)-estratrien-17β-ol, m.p. 149.9° C.

$[α]_D^{20} = +76.4°$ (c=0.500 in chloroform).

Method B

Under nitrogen, 0.040 g. of 17α-ethynyl-C-homo-1,3,5(10)-estratriene-3,17β-diol (prepared according to Example 11) is refluxed in 5 ml. of acetone with 0.100 g. of anhydrous potassium carbonate and 0.5 ml. of methyl iodide for 7 hours. After the mixture has been worked up as described in Example 5, 0.026 g. of the same compound is obtained as if following method A.

EXAMPLE 13

Under an inert gas atmosphere, 0.100 g. of 17α-ethynyl-C-homo-1,3,5(10)-estratriene-3,17β-diol is stirred in 10 mm of anhydrous acetone with 0.500 g. of anhydrous potassium carbonate for 10 minutes. Then 1 ml. of a 10 ml. solution of 2.3 g. of 2-propanesulfonic acid chloride and anhydrous ether is added thereto, and the mixture is stirred for 4 hours at room temperature. The mixture is then concentrated to half its quantity, combined with water, and shaken out with ether. The organic phase, which has been washed with water, is dried over magnesium sulfate and concentrated.

Yield: 0.096 g. of 17α-ethynyl-3-isopropylsulfonyloxy-C-homo-1,3,5(10)-estratrien-17β-ol as a hard foam.

UV [in methanol]: 267 (700), 276 nm. (ε=670)
IR [in KBr]: 3290 (≡C-H), 2120 (C≡C), 1360, 1180 cm$^{-1}$ (SO$_2$).

EXAMPLE 14

0.250 g. of 3-acetoxy-C-homo-1,3,5(10)-estratrien-17-one and 0.100 g. of p-toluenesulfonic acid are dissolved in 2 ml. of freshly distilled isopropenyl acetate and heated to boiling for 2 hours under nitrogen. The mixture is concentrated almost to dryness under vacuum at a bath temperature of 40° C. Again 1 ml. of isopropenyl acetate, as well as 0.050 g. of p-toluenesulfonic acid are added thereto, and the mixture is refluxed for another hour under nitrogen. After cooling to room temperature, 0.15 ml. of pyridine is added, the mixture is diluted with ether and washed in succession with saturated sodium dihydrogen carbonate solution and water, dried over magnesium sulfate, and evaporated. The C-homo-estronenol diacetate is separated from the starting material by gradient chromatography on 20 g. of silica gel with methylene chloride against methylene chloride/acetone (80:20), and stored in a freezer under the exclusion of moisture. The mono- and enol diacetate mixture is afteracetylated and purified by chromatography, thus obtaining 0.225 g. of oily 3,17-diacetoxy-C-homo-1,3,5(10),16-estratetraene which, dissolved in 5 ml. of methylene chloride, is stirred for 1 hour at room temperature with 0.550 g. of anhydrous sodium sulfate, 0.085 g. of anhydrous sodium acetate, and 0.5 ml. of 40% peracetic acid. After dilution with methylene chloride, the mixture is washed with iron)II) sulfate solution and water, dried over magnesium sulfate, and the residue from the evaporation is taken up in 4 ml. of tetrahydrofuran. A suspension is prepared from 0.050 g. of lithium aluminium hydride in 3 ml. of tetrahydrofuran. Under a nitrogen atmosphere the crude 3,17-diacetoxy-16α,17α-epoxy-C-homo-1,3,5(10)-estratriene dissolved in 4 ml. of tetrahydrofuran is added dropwise within 5 minutes and then heated under reflux for 1 hour.

After cooling to room temperature, 0.05 ml. of water, 0.05 ml. of 15% sodium hydroxide solution, and 0.15 ml. of water are added in succession to the reaction mixture. The precipitate is filtered off and washed repeatedly with ether. The residue from the evaporation is purified by preparative layer chromatography, thus obtaining 0.063 mg. of C-homo-1,3,5(10)-estratriene-3,16α,17α-triol as a colorless oil.

UV [in methanol]: 280 nm. (ε=2,100)
IR [in KBr]: 3500, 3440 (O-H), 1605, 1500 (aromat. C=C), 1060 cm$^{-1}$ (C-O).

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A C-homoestratriene of the formula

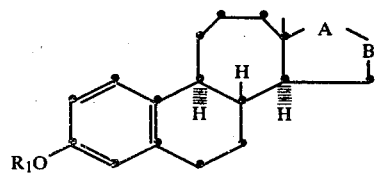

wherein $\overset{A}{\underset{B}{\diagdown}}$ is

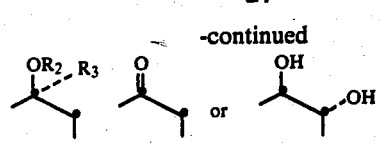

R₁ and R₂ are the same or different, and each is hydrogen, a conventional physiologically compatible acyl group derived from a hydrocarbon carboxylic or sulfonic acid, $C_{1-5}$alkyl, $C_{3-8}$cycloalkyl or tetrahydropyranyl, and R₃ is hydrogen, ethynyl or chloroethynyl.

2. C-Homoestradiol, a compound of claim 1.

3. 3-Acetoxy-C-homo-1,3,5(10)-estratrien-17β-ol, a compound of claim 1.

4. 3-Acetoxy-C-homo-1,3,5(10)-estratrien-17-one, a compound of claim 1.

5. C-Homoestrone, a compound of claim 1.

6. 3-Methoxy-C-homo-1,3,5(10)-estratrien-17-one, a compound of claim 1.

7. 17β-Valeryloxy-C-homo-1,3,5(10)-estratrien-3-ol, a compound of claim 1.

8. 17β-Heptanoyloxy-C-homo-1,3,5(10)-estratrien-3-ol, a compound of claim 1.

9. 17β-Undecanoyloxy-C-homo-1,3,5(10)-estratrien-3-ol, a compound of claim 1.

10. 17β-(3-Cyclopentylpropionyloxy)-C-homo-1,3,5(10)-estratrien-3-ol, a compound of claim 1.

11. 3-Benzoyloxy-C-homo-1,3,5(10)-estratrien-17β-ol, a compound of claim 1.

12. 17α-Ethynyl-C-homo-1,3,5(10)-estratriene-3,17β-diol, a compound of claim 1.

13. 17α-Ethynyl-3-methoxy-C-homo-1,3,5(10)-estratrien-17β-ol, a compound of claim 1.

14. 17α-Ethynyl-3-isopropylsulfonyloxy-C-homo-1,3,5(10)-estratrien-17β-ol, a compound of claim 1.

15. C-Homo-1,3,5(10)-estratriene-3,16α,17β-triol, a compound of claim 1.

16. A pharmaceutical composition comprising an estrogenically effective amount of a compound of claim 1 and a pharmaceutically acceptable carrier.

17. The pharmaceutical composition of claim 16 which further comprises a progestogenically effective amount of a progestogen.

18. A method for contraception which comprises administering to a mammal a contraceptively effective amount of a compound of claim 1.

19. A method for treating estrogen deficiency which comprises administering to a mammal an amount of a compound of claim 1 effective to lessen the deficiency.

* * * * *